US012697413B2

(12) United States Patent
Lee et al.

(10) Patent No.: US 12,697,413 B2
(45) Date of Patent: Aug. 4, 2026

(54) METHOD FOR COATING IMPLANT USING HEAT

(71) Applicants: SEOUL NATIONAL UNIVERSITY R&DB FOUNDATION, Seoul (KR); BS RESEARCH CO., LTD., Seoul (KR)

(72) Inventors: Yan Lee, Seoul (KR); Sun Ah Kang, Seoul (KR); Tae Hyun Choi, Seoul (KR); Ji Ung Park, Gwangju (KR); Seul Ah Kim, Namyangju-si (KR); Jung Ah Kim, Ansan-si (KR); Mi Ok Kim, Seoul (KR); Young Min Kim, Gimpo-si (KR); Xian Jin, Seoul (KR); Wufuer Maierdanjiang, Seoul (KR); Gee Ho Park, Namyangju-si (KR); Byoung Jun Jeon, Seoul (KR); Eun Jung Choi, Seoul (KR); Yan Huang, Seoul (KR)

(73) Assignees: SEOUL NATIONAL UNIVERSITY R&DB FOUNDATION, Seoul (KR); BS RESEARCH CO., LTD., Seoul (KR)

( * ) Notice: Subject to any disclaimer, the term of this patent is extended or adjusted under 35 U.S.C. 154(b) by 0 days.

(21) Appl. No.: 17/610,418

(22) PCT Filed: May 7, 2020

(86) PCT No.: PCT/KR2020/005998
§ 371 (c)(1),
(2) Date: Nov. 10, 2021

(87) PCT Pub. No.: WO2020/231073
PCT Pub. Date: Nov. 19, 2020

(65) Prior Publication Data
US 2022/0218872 A1    Jul. 14, 2022

(30) Foreign Application Priority Data
May 10, 2019    (KR) ........................ 10-2019-0055173

(51) Int. Cl.
*A61L 27/34* (2006.01)
*B05D 3/00* (2006.01)
(Continued)

(52) U.S. Cl.
CPC .............. *A61L 27/34* (2013.01); *B05D 3/007* (2013.01); *B05D 3/0254* (2013.01); *B05D 3/067* (2013.01);
(Continued)

(58) Field of Classification Search
CPC .............. A61L 27/34; A61L 2300/802; A61L 2420/02; A61L 2430/04; C09D 7/63;
(Continued)

(56) References Cited

U.S. PATENT DOCUMENTS

2002/0133072 A1    9/2002    Wang et al.
2004/0121037 A1    6/2004    Rouns et al.
(Continued)

FOREIGN PATENT DOCUMENTS

CN    101785874 A    7/2010
EP    3132810 A1 *    2/2017    ........... A61F 2/0059
(Continued)

OTHER PUBLICATIONS

Lim et al. "Developing a thermal grafting process for zwitterionic polymers on cross-linked polyethylene with geometry-independent grafting thickness" Acta Biomaterialia 85 (2019) 180-191, available online on Dec. 21, 2018.*
(Continued)

*Primary Examiner* — Robert S Walters, Jr.
(74) *Attorney, Agent, or Firm* — Seed Intellectual Property Law Group LLP

(57)    ABSTRACT

Provided is a method for coating an implant using heat, and more particularly to a method for coating only the surface of an implant with a biocompatible polymer by using heat while maintaining physical characteristics of the implant. The method for coating an implant using heat according to the present invention may effectively introduce a biocom-
(Continued)

patible polymer onto a three-dimensional material surface and thus may overcome the spatial limitations of light, and enables mass-coating and thus may be effectively used in the manufacture of an implant coated with a biocompatible polymer.

8 Claims, 14 Drawing Sheets

(51) Int. Cl.

| | |
|---|---|
| *B05D 3/02* | (2006.01) |
| *B05D 3/06* | (2006.01) |
| *C08J 7/06* | (2006.01) |
| *C09D 4/00* | (2006.01) |
| *C09D 7/63* | (2018.01) |

(52) U.S. Cl.
CPC .................................... *C08J 7/06* (2013.01); *C09D 4/00* (2013.01); *C09D 7/63* (2018.01); *A61L 2300/802* (2013.01); *A61L 2420/02* (2013.01); *A61L 2430/04* (2013.01); *C08J 2433/14* (2013.01)

(58) Field of Classification Search
CPC ........ C09D 4/00; B05D 3/007; B05D 3/0254; B05D 3/067; C08J 7/06; C08J 2433/14
See application file for complete search history.

(56) References Cited

U.S. PATENT DOCUMENTS

| | | |
|---|---|---|
| 2011/0305872 A1 | 12/2011 | Li et al. |
| 2015/0056411 A1 | 2/2015 | Zhang et al. |
| 2017/0035555 A1 | 2/2017 | Choi et al. |

FOREIGN PATENT DOCUMENTS

| | | |
|---|---|---|
| JP | 2003-510378 A | 3/2003 |
| KR | 10-2013-0074226 A | 7/2013 |
| KR | 10-2015-0121270 A | 10/2015 |

OTHER PUBLICATIONS

Goda et al., "Biomimetic phosphorylcholine polymer grafting from polydimethylsiloxane surface using photo-induced polymerization", Biomaterials, vol. 27, pp. 5151-5160, 2006.

* cited by examiner

METHOD FOR COATING IMPLANT USING HEAT

TECHNICAL FIELD

The present invention relates to a method for coating an implant using heat, and more particularly to a method for coating only the surface of an implant with a biocompatible polymer by using heat while maintaining physical characteristics of the implant.

BACKGROUND ART

As society becomes more sophisticated and aging, there is an emerging need to develop various biomaterials to provide artificial tissue and organs transplanted into living organisms. Accordingly, despite multilateral efforts made to develop various biomaterials, applicable biocompatible substances are still limited, and side effects are often caused by commercially available substances. Capsular contracture is a representative side effect occurring in the case where an implant used in cosmetic surgery for breast augmentation/reconstruction is implanted into the human body. Since the surfaces of implants widely used for cosmetic breast surgery are of a substance called polydimethylsiloxane (PDMS) having chemical properties different from actual breast tissue, about 17.5% of patients who have received breast augmentation/reconstruction surgery experience a side effect called capsular contracture in which abnormal fibrous tissue surrounds the implants. When such side effects occur, there is no special treatment for the side effect, except for surgical removal. Even if surgical removal is performed, it is not easy to completely remove the implant, or serious after-effects may occur in cases of severe cellular adsorption of tissue to the surface of the implant. Such side effects not only cause pain in patients, but also mentally/economically reduce patients' quality of life and result in increased medical expenses due to increased costs of treatment and management, leading to socioeconomic loss.

As described above, once an implant is inserted into the human body, a capsule is formed as a defense mechanism of the body to separate a foreign body from tissue, and excessive capsular contracture leads to thickening of collagen-fiber capsule due to a response in the living body, causing pain and deformation of the implant. Because many implants inserted from the outside are recognized as foreign substances in the living body, various proteins contained in body fluids are adsorbed thereto, and various subsequent biochemical processes are accompanied by thrombus formation, immune response, tissue deformation, necrosis, and/or degeneration. Therefore, for accomplishing a biocompatible implant as well as reducing capsular contracture, the most important factor is to prevent the surface of the implant from being recognized as a foreign substance by coating the surface of the implant with a biocompatible substance. At present, for reduction of capsular contracture caused by excessive in vivo foreign body reaction of the implant, various attempts have been made to change the site of implantation, wash the implant with an antibiotic, use a steroid, and conduct texture processing on the surface of the implant. However, there has been no method of preventing a fundamental mechanism by which the implant is recognized as a foreign object.

Polydimethylsiloxane (PDMS)-based materials, which are used as representative surface materials for implants to be inserted into the human body, have been applied to various medical devices, such as ophthalmic biomaterials, microfluidic devices, artificial lungs, and artificial finger joints, due to high oxygen permeability, excellent mechanical properties, optical transparency, self-sealing ability, convenient processability, and chemical stability. However, intrinsic hydrophobicity and bioadhesion of PDMS, e.g., non-specific protein adsorption to the materials, are major limitations in using PDMS as a biomaterial since thrombus formation, foreign body reaction, bacterial infection, and other undesired reactions are induced thereby. Therefore, there is a need to modify surface properties of PDMS.

A biomimetic synthetic phospholipid polymer, particularly poly(methacryloyloxyethyl phosphorylcholine) (PMPC), which is a polymer of 2-methaacryloyloxyethyl phosphorylcholine (MPC), has a structure similar to a head group of phosphatidyl choline, which is one of the phospholipids constituting the cell membrane of the human body, and thus biocompatibility, hemocompatibility such as anti-thrombotic activity, and anti-adsorption or anti-adhesion activity against proteins or cells may be obtained thereby. Based thereon, the polymer has been studied to be applied to drug delivery and tissue engineering and used as a surface material for diverse biomaterials.

Recently, a study has been conducted on a method of coating an implant by polymerizing a biomimetic polymer using UV light (Goda, T. et al., *Biomaterials;* 2006; Vol. 27). However, the polymerization using UV light is limited by transparency of a material or occurs only on an area directly exposed to light, and there is a problem in that irradiation with light is difficult in a three-dimensionally complex structure.

With this background, as a result of intensive efforts to effectively introduce a durable polymer onto the surface of an implant regardless of an external appearance of a material, the present inventors have found that a biocompatible polymer is effectively introduced by using heat, which can be uniformly applied to a three-dimensional structure and thereby overcome spatial limitations of irradiation with light and enable mass-coating, and confirmed that this method may be effectively used in the manufacture of coated implants, thereby completing the present invention.

DISCLOSURE

Technical Problem

An object of the present invention is to provide a method for coating an implant, the method including: allowing a thermal initiator to adsorb onto an implant; and adding a solution including an acrylate group-containing amphoteric monomer and a crosslinking agent to the implant adsorbed with the thermal initiator and applying heat thereto.

Technical Solution

An aspect of the present invention to achieve the above-described object provides a method for coating an implant, the method including: allowing a thermal initiator to adsorb onto an implant; and adding a solution including an acrylate group-containing amphoteric monomer and a crosslinking agent to the implant adsorbed with the thermal initiator and applying heat thereto.

In the case where an implant is coated using a known method of irradiating a photoinitiator with UV light, there is a problem in that a coating is considerably affected by a three-dimensional shape of a material. However, in the case of using a method of coating an implant using heat according to the present invention, capsular contracture may be inhibited similarly to that shown in the conventional method, and a biocompatible polymer may be effectively applied to various three-dimensional surfaces of materials in comparison with the method using UV light to thereby overcome spatial limitations of irradiation with light.

In a specific embodiment of the present invention, it was confirmed that a water contact angle of the top surface of a disc coated with PMPC crosslinked using light was significantly decreased since hydrophilicity was introduced into only the top surface directly exposed to light, but a water contact angle of the bottom surface, which was not directly exposed to light, was not decreased as much as that of the top surface. On the contrary, it was confirmed that water contact angles of the top and bottom surfaces of a disc coated with PMPC crosslinked using heat were decreased uniformly (FIG. 2). Based thereon, by heat treatment, spatial limitations caused in the case of using light may be overcome, and coating may be effectively introduced without being limited by the three-dimensional shape.

In a specific embodiment of the present invention, while nitrogen and phosphorus were detected from the surface of the disc coated with PMPC crosslinked using light to a depth of 35 nm to 40 nm, nitrogen and phosphorus were detected from the surface of the disc coated with PMPC crosslinked using heat to a depth of 75 nm to 85 nm, and the possibility of detection beyond this depth was confirmed (FIG. 4). Based thereon, it was confirmed that a thicker coating layer may be introduced into the disc coated with PMPC crosslinked using heat compared to the disc coated with PMPC crosslinked using light.

The method for coating an implant according to the present invention includes allowing a thermal initiator to adsorb onto an implant. When the thermal initiator is physically adsorbed onto the surface of the implant, polymerization is promoted on the surface of the implant when compared with a case in which a polymerization solution including an initiator is simply heated.

As used herein, the term "thermal initiator" refers to a material capable of forming a radical upon receiving heat. Therefore, radical polymerization may be induced by applying heat to the thermal initiator to form the radical. The radical polymerization is a polymerization method to form a polymer by continuously adding a free radical, and the radical may generally be formed via various mechanisms by molecules of a separate initiator.

Once the reaction is initiated, the radical forms a stable single bond using one pi bond electron from a monomer of a polymer including a double bond. Thus, as the double bond is converted into the single bond, a new radical including a remaining electron is formed at another carbon atom that does not form a bond with the previous radical. The above-described process is repeated by the newly formed radical, thereby growing a polymer chain.

In the present invention, the thermal initiator may be selected from the group consisting of benzoyl peroxide (BPO), lauroyl peroxide, tert-butyl hydroperoxide, cumene hydroperoxide (CHP), di-tert-butyl peroxide (DTBP), dicumyl peroxide (DCP), azobisisobutyronitrile (AIBN), potassium persulfate (KPS), ammonium persulfate (APS), 2,2'-azobis[2-(2-imidazolin-2-yl)propane]dihydrochloride (VA-044), 2,2'-azobis(2-methylpropionamidine) dihydrochloride (V-50), 2,2'-azobis[N-(2-carboxyethyl)-2-methylpropionamidine]tetrahydrate (VA-057), 2,2'-azobis[2-(2-imidazolin-2-yl)propane](VA-061), 2,2'-azobis[2-methyl-N-(2-hydroxyethyl)propionamide] (VA-086), 4,4'-azobis(4-cyanovaleric acid) (V-501), 2,2-azobis(4-methoxy-2,4-dimethylvaleronitrile) (V-70), 2,2-azobis(2,4-dimethylvaleronitrile) (V-65), dimethyl 2,2'-azobis(2-methylpropionate) (V-601), 2,2-azobis(2-methylbutyronitrile) (V-59), 2,2-azobis(cyclohexane-1-carbonitrile) (V-40), and 2,2'-azobis(N-butyl-2-methylpropionamide) (VAm-110), specifically benzoyl peroxide, without being limited thereto.

In the present invention, the thermal initiator may be used in an amount of 10 mol % to 50 mol %, specifically 15 mol % to 50 mol %, 20 mol % to 50 mol %, 30 mol % to 45 mol %, 35 mol % to 45 mol %, or 38 mol % to 42 mol %, more specifically 40 mol %, based on the acrylate group-containing amphoteric monomer, without being limited thereto.

In the case where the thermal initiator is used in an amount less than the above-described lower limit, i.e., less than 10 mol %, the amount of a polymer generated on the surface, e.g., the number of polymer strands and/or the length (molecular weight) of each polymer strand, significantly decreases such that the surface of the implant may not be sufficiently covered. On the contrary, in the case where the thermal initiator is used in an amount greater than the above-described upper limit, i.e., greater than 50 mol %, samples may be wasted unnecessarily.

As used herein, the term "implant", also referred to as "implant for insertion into a living body", means a structure inserted into a living body for rebuilding or replacing damaged or lost biological tissue, for cosmetic purposes, or for therapeutic purposes, specifically an implant for augmentation or reconstruction of a breast, but is not limited thereto. In addition, the implant may be in the form of a solid structure or a pouch-type structure with fluidity, without being limited thereto.

Since the coating of the present invention is formed by covalent bonds between acrylate groups of the acrylate group-containing amphoteric monomer and the external surface of the implant, the implant that is coated by way of the coating method of the present invention may include a functional group capable of providing a radical that forms a bond with an end of the amphoteric monomer including a C=C bond of the acrylate group such that the acrylate group-containing amphoteric monomer as one component of the polymerization solution forms a covalent bond with the external surface of the implant via the end including the C=C bond of the acrylate group. Any materials used for implants known in the art except for metals and hydrophilic ethylene-based materials may be used without limitation.

In the present invention, the implant may include a surface material selected from the group consisting of polydimethylsiloxane (PDMS), hydroxyapatite (HA), polylactic acid (PLA), polyglycolic acid (PGA), polytetrafluoroethylene (PTFE), polyethylene terephthalate (PET), polypropylene, polyamide, polyacetal, polyester, and polymethyl methacrylate, specifically a surface material of polydimethylsiloxane (PDMS), without being limited thereto.

The coating method of the present invention includes adding a solution including an acrylate group-containing amphoteric monomer and a crosslinking agent to the implant adsorbed with the thermal initiator and applying heat thereto. In the case where polymerization is performed using heat as described above, a biocompatible polymer may be introduced into a three-dimensional surface of a material more effectively than the case where polymerization is performed via irradiation with light, and coating may be performed in large quantities by overcoming spatial limitations caused by irradiation with light.

The solution including an acrylate group-containing amphoteric monomer and a crosslinking agent is also referred to as a polymerization solution.

As used herein, the term "acrylate group-containing amphoteric monomer" refers to an acrylate-based monomer having zwitterionic properties due to inclusion of a cation and an anion in a single molecule. Since a material having zwitterionic properties forms strong hydrogen bonds with water molecules via its cationic and anionic charges, a hydrated layer may be formed around the material to thereby effectively inhibit non-specific adhesion of proteins or cells. Such inhibition of non-specific adhesion by the amphoteric material may lead to reduction in a series of responses such as thrombus formation, immune response, tissue deformation, and fibrous capsule formation occurring in the case of inserting an implant into a living body.

In the present invention, the acrylate group-containing amphoteric monomer is not limited to a specific formula and may include any acrylate-based monomer including at least one selected from the group consisting of phosphorylcholine (PC) including phosphorus and nitrogen, sulfobetaine (SB) including sulfur and nitrogen, and carboxybetaine (CB) including carbon and nitrogen, regardless of linkage type. Specifically, the acrylate group-containing amphoteric monomer may include at least one selected from the group consisting of methacryloyloxyethyl phosphorylcholine (MPC), acryloyloxyethyl phosphorylcholine (APC), sulfobetaine methacrylate, sulfobetaine acrylate, carboxybetaine methacrylate, and carboxybetaine acrylate, and more specifically, it may be methacryloyloxyethyl phosphorylcholine, but is not limited thereto.

In the present invention, the crosslinking agent may be one selected from the group consisting of dipentaerythritol pentaacrylate, dipentaerythritol hexaacrylate, ethyleneglycol diacrylate, ethyleneglycol dimethacrylate, allyl methacrylate, acetoacetoxyethyl methacrylate, isocyanatoethyl methacrylate, isobutylmethacrylate, n-butylmethacrylate, and any combination thereof, specifically dipentaerythritol pentaacrylate or dipentaerythritol hexaacrylate, without being limited thereto.

In the present invention, the crosslinking agent may be used in an amount of 0.01 mol % to 2.0 mol %, specifically 0.01 mol % to 2.0 mol %, 0.1 mol % to 1.8 mol %, 0.5 mol % to 1.5 mol %, 0.8 mol % to 1.2 mol %, 0.9 mol % to 1.1 mol %, and more specifically 1.0 mol % based on the phosphorylcholine having an acrylate group, without being limited thereto.

In the case where the crosslinking agent is used in an amount less than the above-described lower limit, i.e., less than 0.01 mol %, crosslinking may not be sufficiently performed such that desired physical properties may not be obtained, a desired strength of the coating may not be obtained, or the coating may be peeled off during a washing process. On the contrary, in the case where the crosslinking agent is used in an amount greater than the above-describe upper limit, i.e., greater than 2.0 mol %, the implant may not have a desired elasticity and may be over-cured due to excessive crosslinking, and samples may be wasted unnecessarily.

In the present invention, heat may be applied by using any method well known in the art without limitation, specifically using a pre-heated oil bath, but is not limited thereto.

In the present invention, temperature at which heat is applied may vary according to a type of the implant, sensitivity thereof to heat, and the like, which may be appropriately selected by those of ordinary skill in the art. In addition, a time during which heat is applied may vary according to temperature of heat treatment and may also be appropriately selected by those of ordinary skill in the art.

Specifically, the heat may be applied at a temperature of 60° C. to 100° C., specifically 60° C. to 95° C., 65° C. to 90° C., 65° C. to 85° C., 65° C. to 75° C., 68° C. to 73° C., 69° C. to 71° C., 65° C. to 99° C., 70° C. to 98° C., 75° C. to 97° C., 80° C. to 96° C., 85° C. to 95° C., 90° C. to 94° C., 91° C. to 93° C., 65° C. to 95° C., or 70° C. to 92° C., and more specifically 70° C. or 92° C., without being limited thereto.

Specifically, the heat may be applied for 1 to 18 hours, specifically 1 to 17 hours, 1 to 16 hours, 1 to 15 hours, 1 to 12 hours, 1 to 10 hours, 1 to 8 hours, 1 to 5 hours, 1 to 3 hours, 3 to 17 hours, 5 to 17 hours, 8 to 17 hours, 10 to 17 hours, 12 to 17 hours, or 15 to 17 hours, and more specifically 1.5 hours or 16 hours, without being limited thereto.

More specifically, the step of allowing the thermal initiator to adsorb onto the implant of the present invention may include: immersing the implant in an initiator solution including the thermal initiator and a crosslinking agent; and drying the implant.

The adding of the solution including an acrylate group-containing phosphorylcholine (PC) monomer and a crosslinking agent to the implant adsorbed with the thermal initiator and applying heat thereto may include: immersing the implant adsorbed with the thermal initiator in a solution including an acrylate group-containing phosphorylcholine (PC) monomer and a crosslinking agent; and applying heat thereto.

Advantageous Effects

The method for coating an implant using heat according to the present invention may effectively introduce a biocompatible polymer onto a three-dimensional material surface to thereby overcome the spatial limitations of light and enable mass-coating so that the method may be effectively used in the manufacture of a biocompatible polymer-coated implant.

BEST MODE

Figure 1:
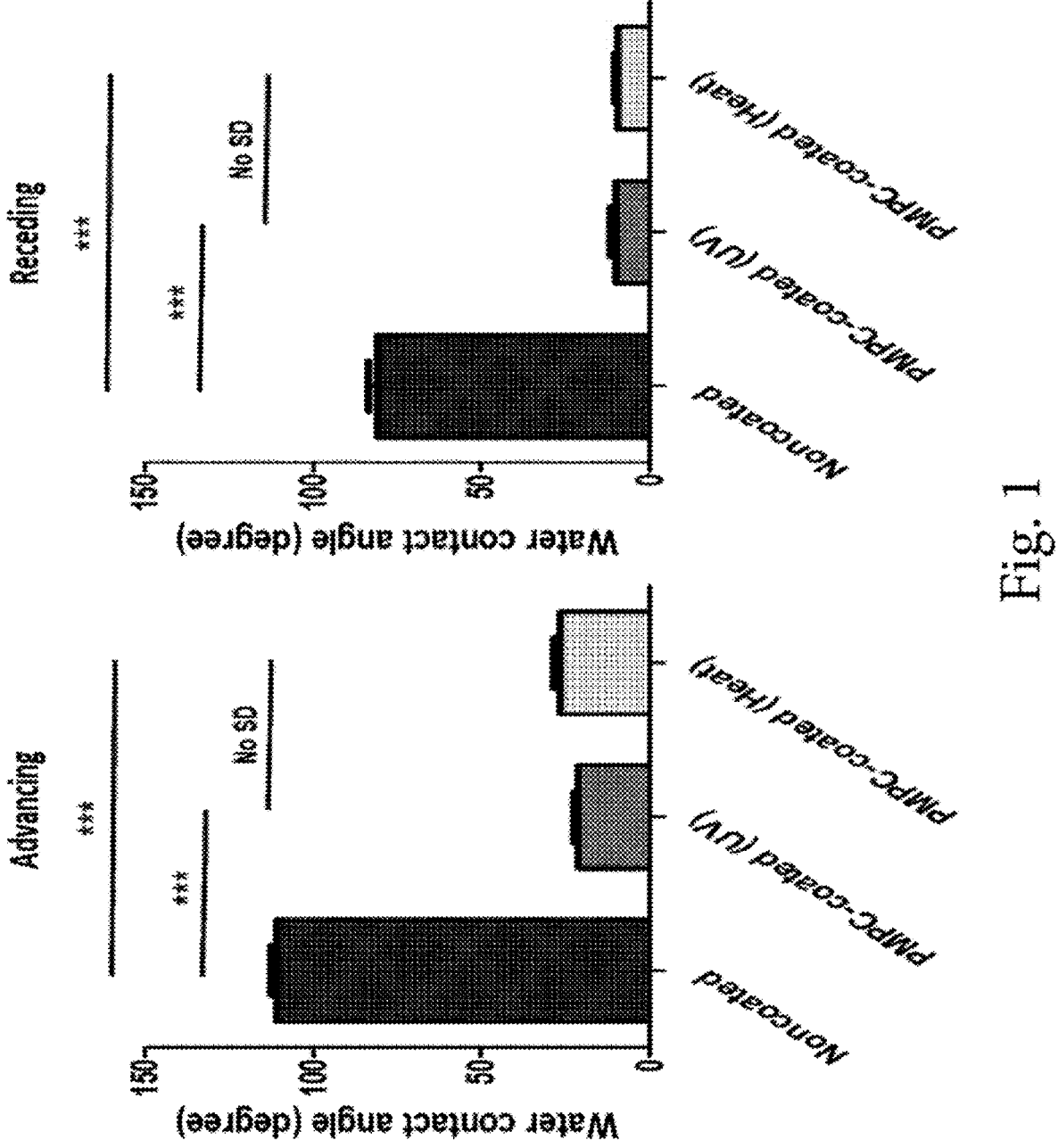
FIG. 1 shows water contact angles of a disc not coated with crosslinked PMPC (non-coated), a disc coated with PMPC crosslinked using light (UV-coated), and a disc coated with PMPC crosslinked using heat (heat-coated).

Hereinafter, the present invention will be described in more detail with reference to the following examples. However, the following examples are merely presented to exemplify the present invention, and the scope of the present invention is not limited thereto.

Example 1. Preparation of Coated Implant

Example 1-1. Preparation of Implant Coated Using Light (Comparative Example)

An initiator solution was prepared by dissolving 0.055 M benzophenone as a photoinitiator and 2.5 mM dipentaerythritol pentaacrylate (or dipentaerythritol hexaacrylate) as a crosslinking agent in an acetone or ethanol solvent. Subsequently, a silicone-filled breast implant (Mentor, 125 cc) was sufficiently immersed in the initiator solution for 1 minute and dried. A polymerization solution was prepared by dissolving 5.0 mM ethyleneglycol dimethacrylate (EGDMA), as a crosslinking agent, and 0.25 M methacryloyloxyethyl phosphorylcholine (MPC), as a monomer, in distilled water. After immersing the implant adsorbed with the initiator in the polymerization solution, UV light was irradiated at a distance of 18.4 cm for 10 minutes such that the implant was coated by way of radical polymerization. The coated implant was cleaned via sonication once for 10 minutes and washed to remove residual reactants before the implant was used for analysis. The cleaning method using ultrasonic waves is a relatively strong method compared to other cleaning methods commonly used in the art. Such a relatively strong method was used herein to mimic peeling of the coating due to movement after in vivo implantation.

Example 1-2. Preparation of Implant Coated Using Heat

An initiator solution was prepared by dissolving 0.1 M benzoyl peroxide, as a thermal initiator, and dipentaerythritol pentaacrylate (or dipentaerythritol hexaacrylate), as a crosslinking agent, in a mixed solvent of MC and acetone (1:1). Subsequently, a silicone-filled breast implant (Mentor, 125 cc) was sufficiently immersed in the initiator solution for 1 minute and dried. A polymerization solution was prepared by dissolving 1 mol % ethylene glycol dimethacrylate (EGDMA), as a crosslinking agent, and 0.25 M methacryloyloxyethyl phosphorylcholine (MPC), as a monomer, in distilled water. After sufficiently immersing the implant adsorbed with the initiator in the polymerization solution, the polymerization solution was heated at 92° C. for 90 minutes or at 70° C. for 16 hours using a preheated oil bath such that the implant is coated by way of radical polymerization. The coated implant was cleaned via sonication once for 10 minutes and washed to remove residual reactants before the implant was used for analysis. The cleaning method using ultrasonic waves is a relatively strong method compared to other cleaning methods commonly used in the art. Such a relatively strong method was used herein to mimic peeling of the coating due to movement after in vivo implantation.

Example 2. Analysis of Properties of Coated Surface

In order to analyze properties of the coated surface of the implant, a Sylgard® 184 silicone disc (Dow Corning) formed of polydimethylsiloxane (PDMS) which has the same chemical structure as the surface of the implant was cured to prepare a circular disc having a diameter of 15 mm, and the disc was coated in the same manner as in Example 1.

Example 2-1. Analysis of Change in Water Contact Angle of Coated Surface

Changes in hydrophilicity of a disc not coated with crosslinked PMPC (non-coated), a disc coated with PMPC crosslinked using light (UV-coated), and a disc coated with PMPC crosslinked using heat (heat-coated) were identified by measuring water contact angles thereof.

Specifically, among dynamic water contact angle measurement methods, a captive drop method was used to measure advancing contact angles and receding contact angles. The advancing contact angles were obtained by measuring contact angles between the surface and a water droplet while the amount of deionized water on the surface was increased from 0 μL to 6 μL using a needle. The receding contact angles were obtained by measuring contact angles between the surface and a water droplet while the amount of deionized water on the surface was decreased from 6 μL to 3 μL. The advancing contact angle is a numerical value representing hydrophobicity of the surface and the receding contact angle is a numerical value representing hydrophilicity of the surface. In the present invention, information on hydrophilicity of the surface was obtained by observing changes in the advancing contact angles and the receding contact angles. Water contact angles determined based on the obtained information are shown in FIG. 1.

As shown in FIG. 1, since the non-coated disc used as a negative control has high hydrophobicity, high water contact angles were observed in the advancing contact angles and the receding contact angles. However, it was confirmed that the water contact angles significantly decreased in the discs coated with PMPC crosslinked using light and heat compared with the non-coated disc. That is, it could be seen that the surface was modified to have hydrophilicity by coating with the crosslinked PMPC, and the disc coated using heat also had the surface modified in a degree similar to that of the disc coated using light.

Example 2-2. Analysis of Water Contact Angle of Top/Bottom of Coated Surface Differences in coating effects according to three-dimensional shapes of the disc coated with PMPC crosslinked using light (UV-coated) and the disc coated with PMPC crosslinked using heat (heat-coated) were identified using water contact angles.

Figure 2:
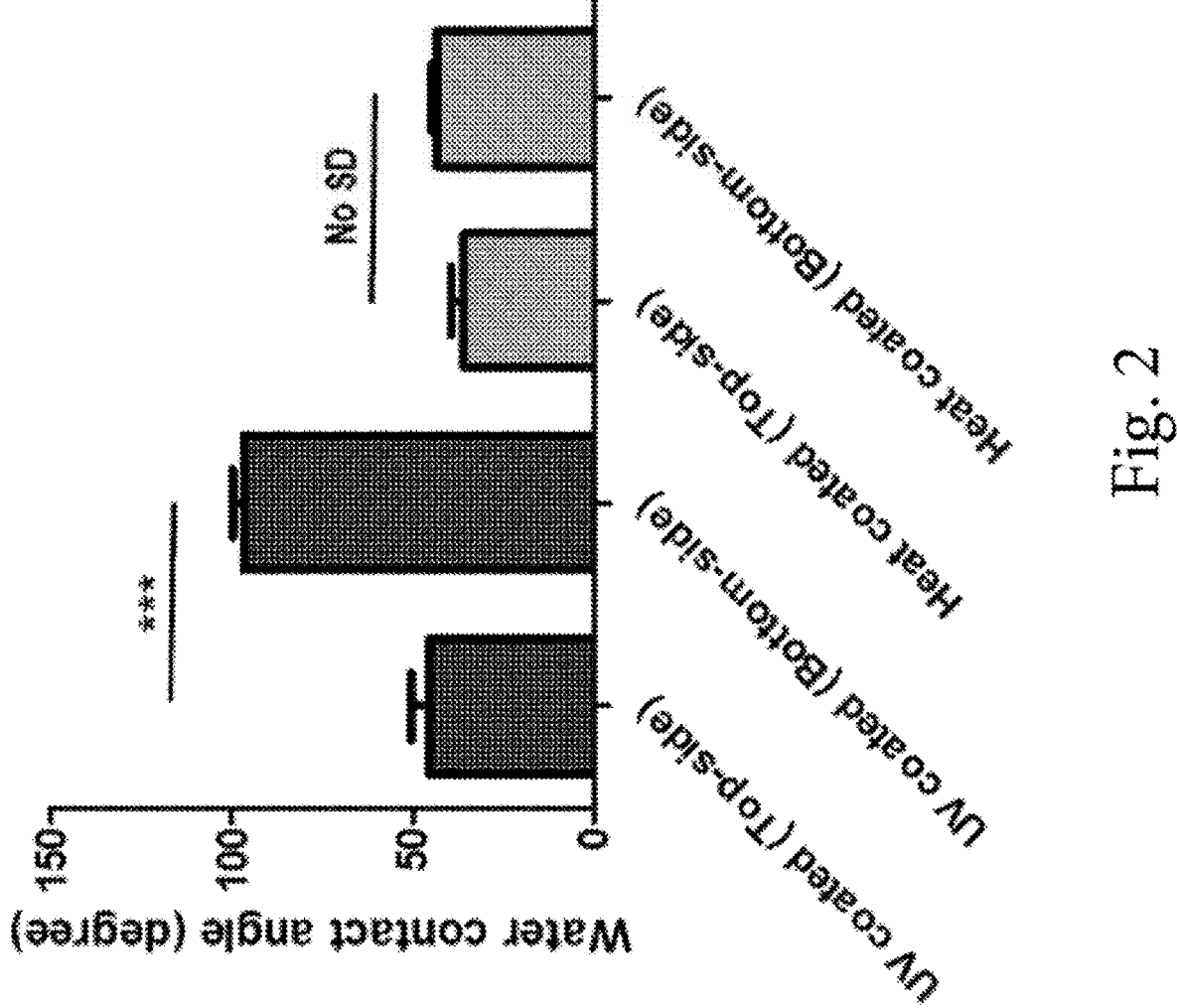
FIG. 2 shows water contact angles of top and bottom surfaces of a disc coated with PMPC crosslinked using light (UV-coated), and a disc coated with PMPC crosslinked using heat (heat-coated).

As shown in FIG. 2, since coating is limited by a spatial shape of a material to be coated in the disc coated with PMPC crosslinked using light, hydrophilicity was introduced into only the top surface which was directly exposed to light, and thus a water contact angle of the top surface of the disc coated with PMPC crosslinked using light was significantly decreased. However, a water contact angle of the bottom surface, which was not directly exposed to light, was not decreased as much as that of the top surface. On the contrary, the water contact angles of the top and bottom surfaces of the disc coated with PMPC crosslinked using heat were decreased uniformly, indicating that spatial limitations caused in the case of using light may be overcome, and coating may be effectively introduced without being limited by the three-dimensional shape.

Example 2-3. Elemental Analysis of Coated Surface

Figure 3:
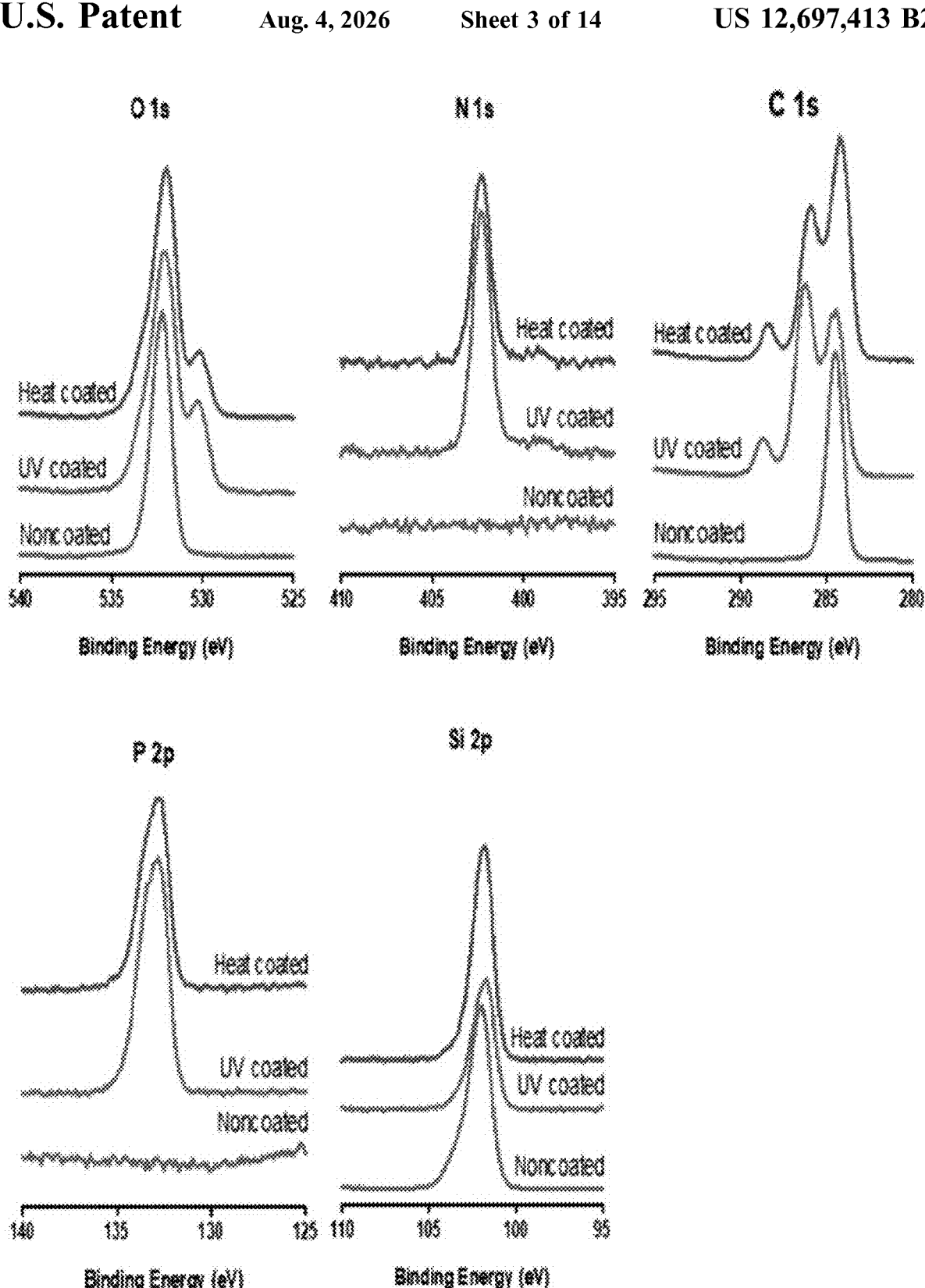
FIG. 3 shows results of analyzing surface elements on the surfaces of a disc not coated with crosslinked PMPC, a disc coated with PMPC crosslinked using light, and a disc coated with PMPC crosslinked using heat.

In order to identify whether changes in water contact angle, i.e., degree of hydrophilicity, which are confirmed in Example 2-1, are caused by introduction of a phosphorylcholine group, surface elements were analyzed using XPS, and the results are shown FIG. 3.

As shown in FIG. 3, while the oxygen content of the surface of the disc coated with PMPC crosslinked using light or heat was maintained at the same level as that of the surface of the non-coated disc, the contents of carbon and/or silicon were significantly reduced. Specifically, in the carbon peaks, while peaks of methylene and/or methyl significantly decreased, peaks of —C—O— and —C=O bonds began to form. Furthermore, the contents of nitrogen and phosphorus, which had not been detected in PMPC, significantly increased. With regard to the analysis results of changes in the water contact angles confirmed in Example 3-1 above, a decrease in the water contact angle, i.e., an increase in hydrophilicity, is consistent with increases in contents of oxygen, nitrogen, and/or phosphorus which have relatively high electronegativity on the surface. This indicates an increase in the content of the phosphorylcholine group including these elements.

In addition, the results described above indicate that the coating with crosslinked PMPC according to the method of the present invention is not damaged even by strong stimulation.

Figure 4:
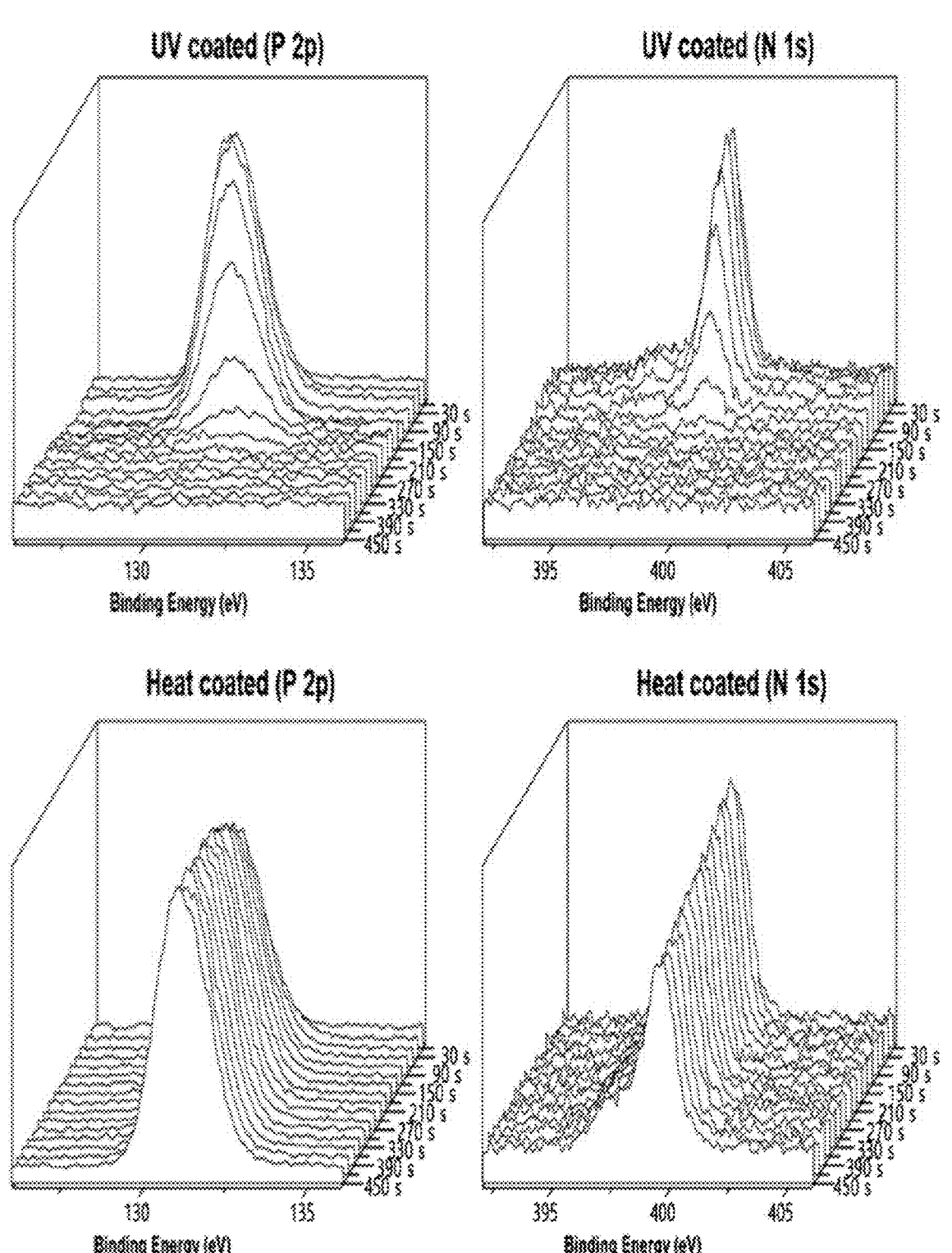
FIG. 4 shows results of analyzing surface elements on the surfaces of a disc not coated with crosslinked PMPC, a disc coated with PMPC crosslinked using light, and a disc coated with PMPC crosslinked using heat, with respect to depth.

In addition, as shown in FIG. 4, in elemental analysis performed with respect to a depth from the surface, while nitrogen and phosphorus were detected from the surface of the disc coated with PMPC crosslinked using light to a depth of 35 nm to 40 nm, nitrogen and phosphorus were detected from the surface of the disc coated with PMPC crosslinked using heat to a depth of 75 nm to 85 nm, and the possibility of detection beyond this depth was confirmed. This indicates that a thicker coating layer may be introduced onto the disc coated with PMPC crosslinked using heat compared to the disc coated with PMPC crosslinked using light.

Example 3. Analysis of Change in Pressure Resistance of Coated Implant

Changes in mechanical strengths of an implant not coated with crosslinked PMPC (non-coated), an implant coated with PMPC crosslinked using light (UV-coated), and an implant coated with PMPC crosslinked using heat (heat-coated) were identified by using a universal testing machine. A load generated by pressing thereon at a rate of 5 mm/min using a 5 kN load cell was measured.

Figure 5:
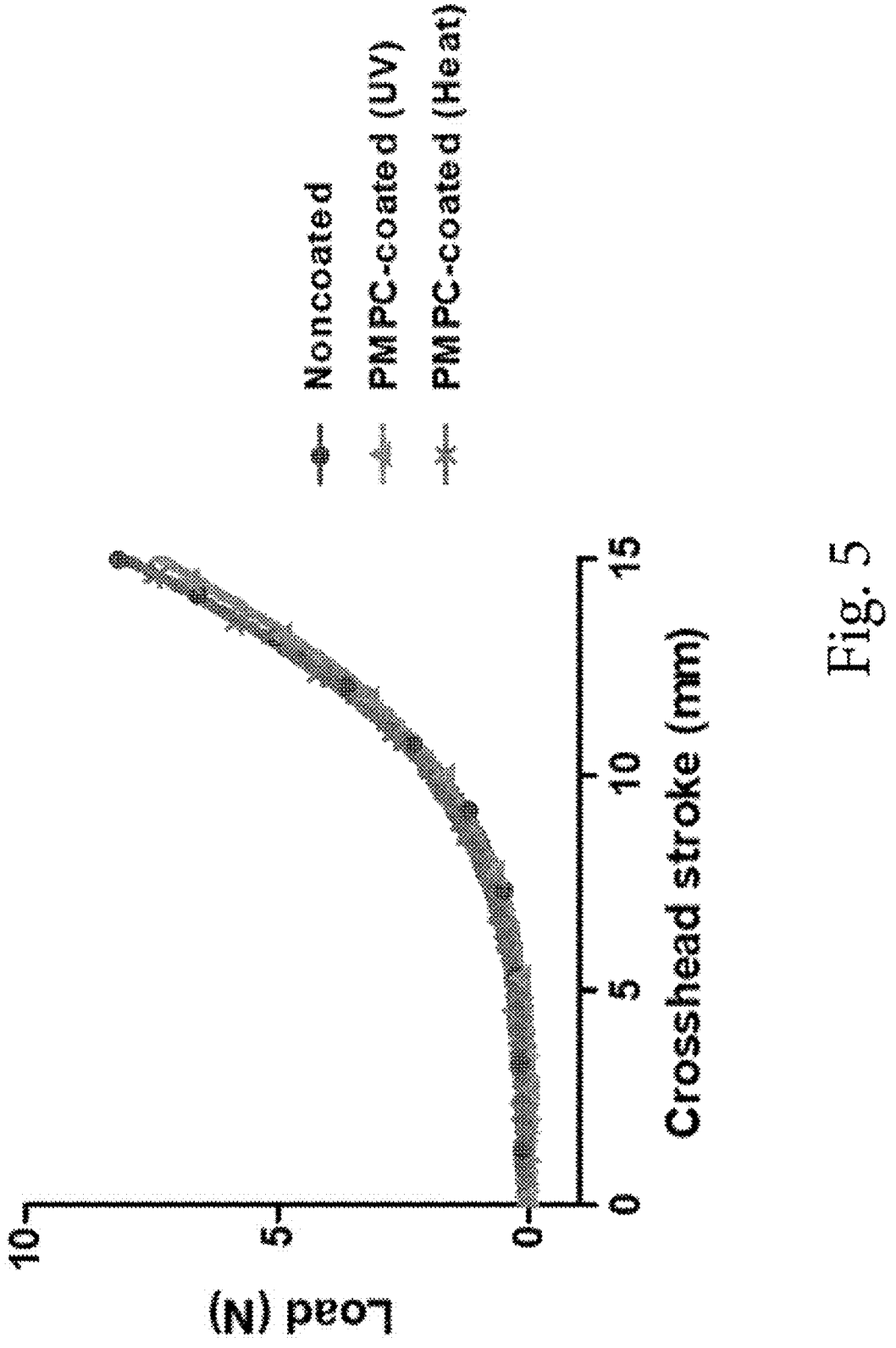
FIG. 5 shows changes in pressure resistance of an implant not coated with crosslinked PMPC, an implant coated with PMPC crosslinked using light, and an implant coated with PMPC crosslinked using heat.

As shown in FIG. 5, a load of the implant coated with PMPC crosslinked using light or heat was measured similarly to a load of the implant not coated with crosslinked PMPC. This indicates that physical and mechanical properties of the implant may be maintained even though the implant is coated with crosslinked PMPC.

Example 4. Analysis of Protein Adsorption-Inhibiting Property

Protein adsorption-inhibiting properties of surfaces of the disc not coated with crosslinked PMPC (non-coated), the disc coated with PMPC crosslinked using light (UV-coated), and the disc coated with PMPC crosslinked using heat (heat-coated) were identified by BCA assay. As the proteins, bovine serum albumin (BSA) and bovine plasma fibrinogen (BPF) were used. Each of the non-coated disc and the discs coated using light and heat was incubated in BSA having a concentration of 4.5 mg/mL or BPF having a concentration of 0.3 mg/mL at 37° C. for 1 hour, and then PDMS was gently washed twice each using a clean DPBS buffer at 37° C. for 1 minute at 200 rpm. Subsequently, BCA assay was performed to quantify the proteins adsorbed onto the surface. Specifically, a BCA kit of Thermo Scientific was used, and Samples A, B, and C contained in the kit were mixed in a volume ratio of 25:24:1 to prepare an assay solution. The washed PDMS was immersed in a fresh DPBS buffer, and the assay solution was added thereto in the same amount, followed by incubation at 60° C. for 1 hour. Then, absorbance was measured at 570 nm to measure the amounts of proteins adsorbed onto the surface. The results are shown in FIGS. 6 and 7.

Figure 6:
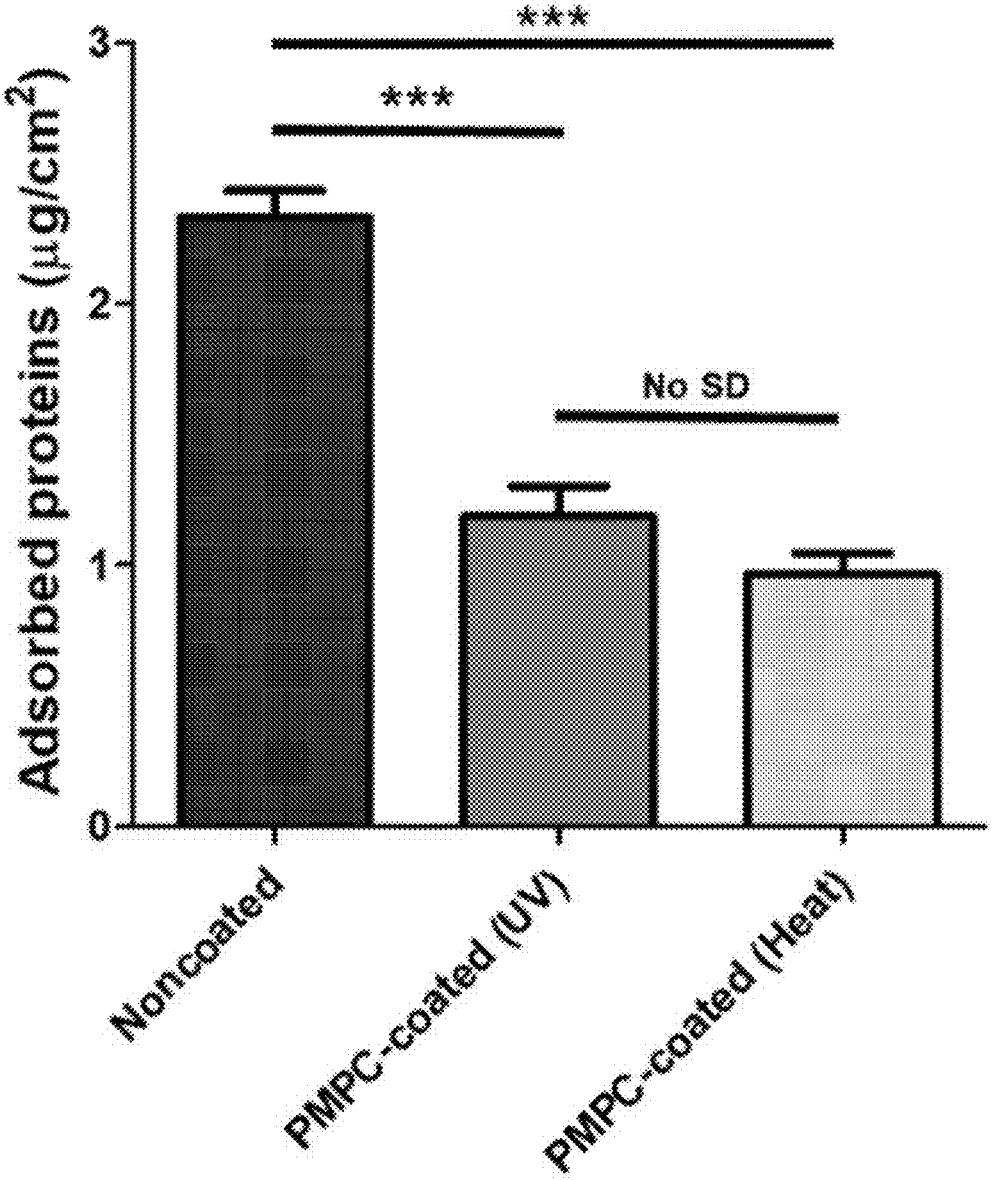
FIG. 6 shows adsorption of BSA on surfaces of a disc not coated with crosslinked PMPC, a disc coated with PMPC crosslinked using light, and a disc coated with PMPC crosslinked using heat.
Figure 7:
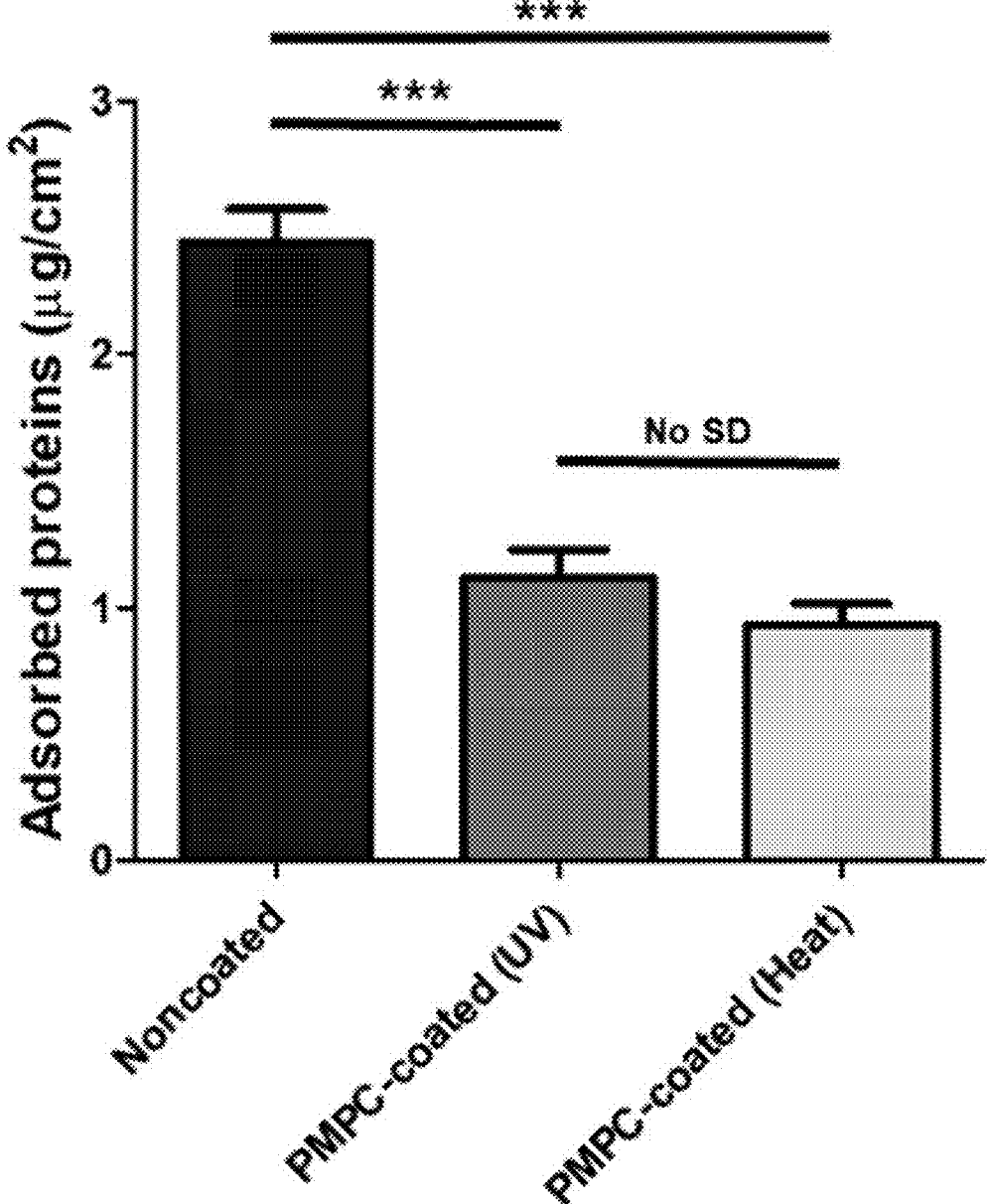
FIG. 7 shows adsorption of BPF on surfaces of a disc not coated with crosslinked PMPC, a disc coated with PMPC crosslinked using light, and a disc coated with PMPC crosslinked using heat.

As shown in FIGS. 6 and 7, adsorption of BSA onto the surface of the disc coated with PMPC using light or heat was decreased compared to the surface of the non-coated disc, and adsorption of BPF onto the surface of the disc coated with PMPC using light or heat was decreased compared to the surface of the non-coated disc. That is, it was confirmed that the adsorption of proteins was significantly decreased on the surfaces of discs coated with crosslinked PMPC in both cases of BSA and BPF when compared to the surface of the non-coated disc.

Example 5. Analysis of Cell Adsorption-Inhibiting Property

Based on the fact that capsular contracture is closely related to hyperproliferation of fibroblasts and collagen formation thereby, fibroblast NIH 3T3 cells were cultured on a disc not coated with crosslinked PMPC (non-coated), a disc coated with PMPC crosslinked using light (UV-coated), and a disc coated with PMPC crosslinked using heat (heat-coated) to identify degrees of cell adsorption. The NIH-3T3 cells were cultured in a DMEM medium containing 10%

FBS in a 5% carbon dioxide environment at 37° C. 30,000 cells were aliquoted per PDMS in a diameter of 1.5 cm, cultured in a 5% carbon dioxide environment at 37° C. for 40 hours, and gently washed with a fresh DMEM medium (containing 10% FBS), followed by a CCK assay. A CCK solution produced by Dojindo Laboratories was used. The washed PDMS was immersed in a fresh DMEM medium (containing 10% FBS), and the CCK solution equivalent to 10% of a volume of the medium was added thereto, followed by incubation in a 5% carbon dioxide environment at 37° C. for 4 hours. Absorbance was measured at 450 nm to measure relative amounts of the cells adsorbed onto the surfaces, and the results are shown in FIG. 8.

Figure 8:
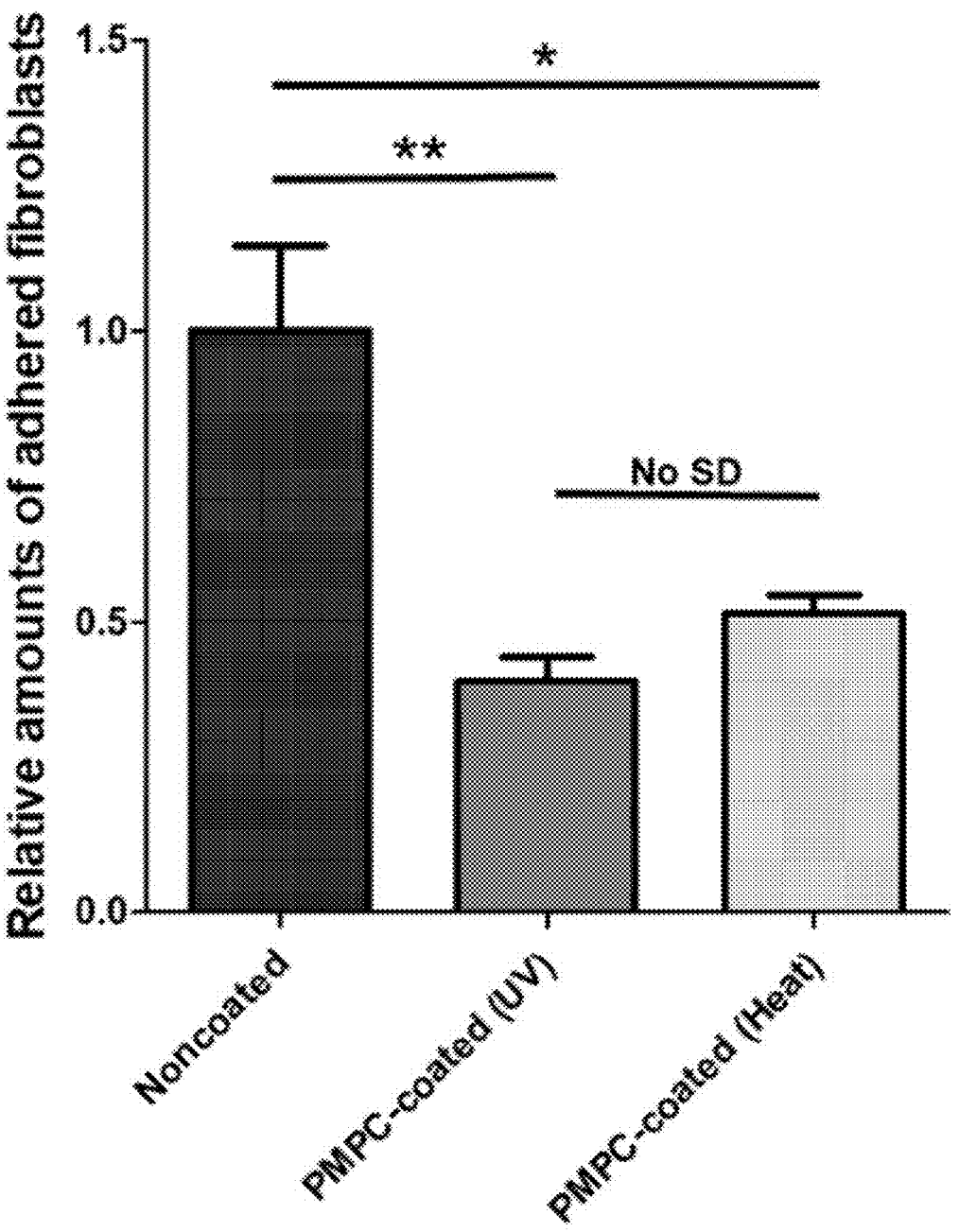
FIG. 8 shows adhesion of fibroblasts on surfaces of a disc not coated with crosslinked PMPC, a disc coated with PMPC crosslinked using light, and a disc coated with PMPC crosslinked using heat.

As shown in FIG. 8, it was confirmed that adsorption of fibroblasts onto the surfaces of the disc coated with PMPC using light or heat was significantly decreased compared to the surface of the non-coated disc.

Example 6. Analysis of In Vivo Response (2-Month Large Animal Experiment)

Four implants not coated with crosslinked PMPC (non-coated) and four implants coated with PMPC crosslinked using heat (heat-coated) were prepared, sterilized using ethanol, and inserted under panniculus *carnosus* muscle of pigs. After 8 weeks (2 months), capsules formed around the inserted implants were collected, and histopathological properties thereof were observed.

Example 6-1. Analysis of In Vivo Capsular Contracture-Inhibiting Activity

In order to identify in vivo capsular contracture-inhibiting activity, top and bottom sides of the capsule around the inserted implant was collected and stained via hematoxylin and eosin (H&E) staining to observe capsular thickness using a microscope. The capsular thickness was measured by dividing the capsule into three portions and measuring capsular thickness of each portion, and the results are shown in FIG. 9.

Figure 9:
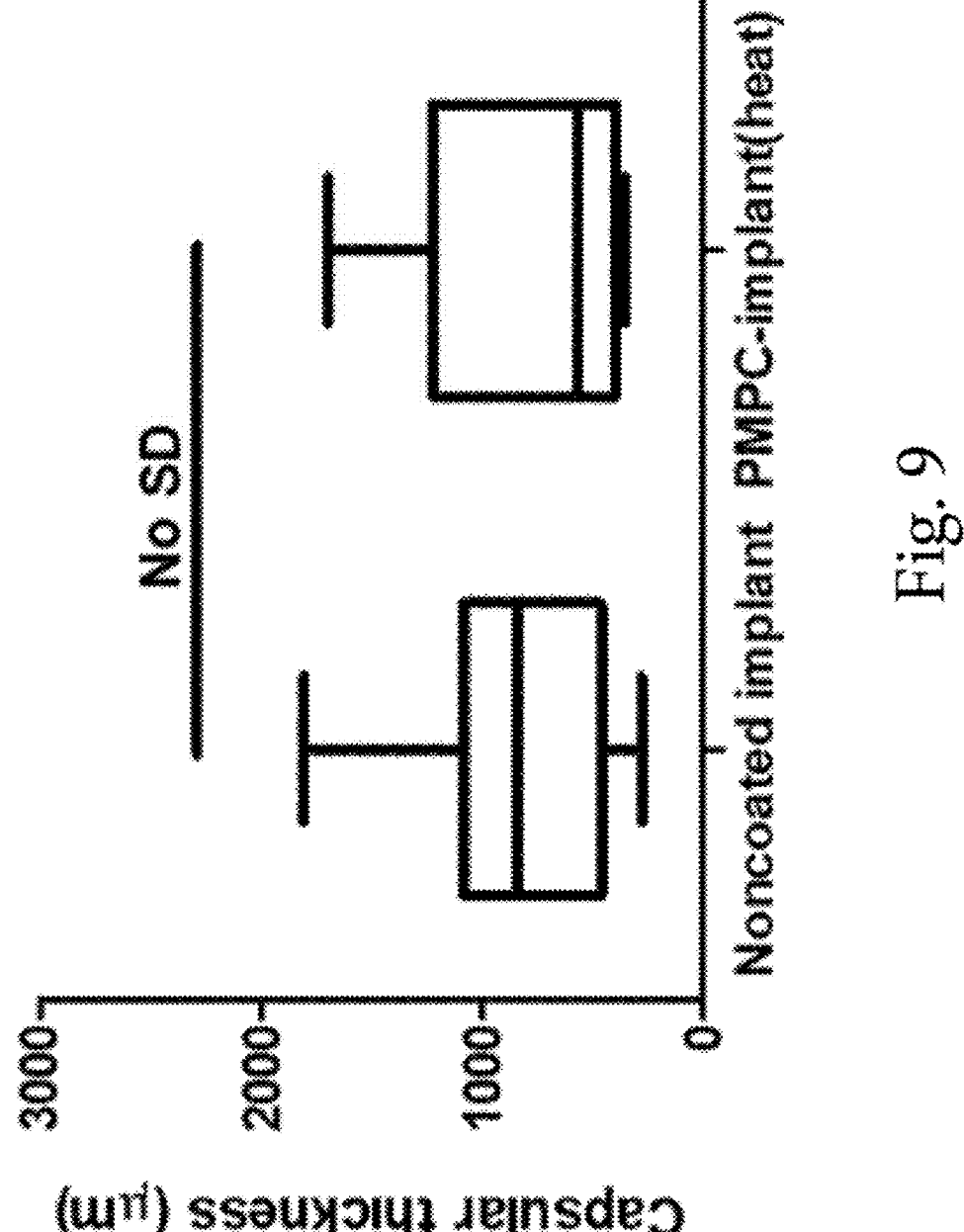
FIG. 9 shows capsular thickness on surfaces of an implant not coated with crosslinked PMPC and an implant coated with PMPC crosslinked using heat at 2 months after insertion into pigs.

As shown in FIG. 9, it was confirmed that an average thickness of the capsule formed on the surface of the implant coated with PMPC crosslinked using heat was decreased compared to an average thickness of the capsule formed on the surface of the non-coated implant.

Example 6-2. Analysis of Cellularity and Vascularity

Cellularity was measured by collecting tissues around the implant, staining the collected tissues, and calculating a sum of scores for inflammation-related cells such as lymphocytes, plasma cells, macrophages, and giant cells. Vascularity was measured by measuring the number of blood vessels via immunohistochemistry (IHC) staining using CD34 as an angiogenesis index. The results are shown in FIG. 10.

Figure 10:
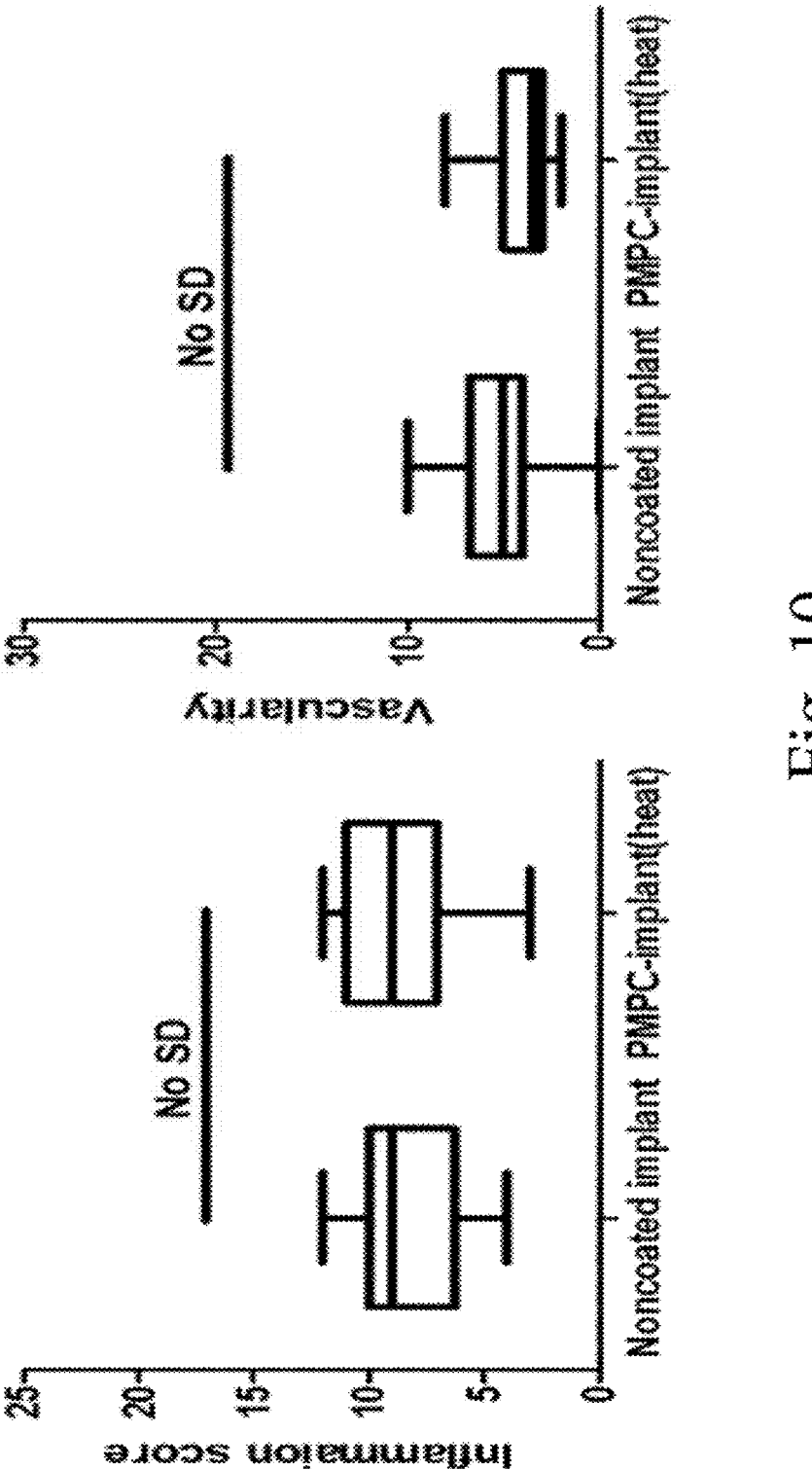
FIG. 10 shows cellularity and vascularity of an implant not coated with crosslinked PMPC and an implant coated with PMPC crosslinked using heat at 2 months after insertion into pigs.

As shown in FIG. 10, it was confirmed that cellularity was similarly observed in both groups, and vascularity of the implant coated with PMPC crosslinked using heat was lower than that of the non-coated implant.

Example 6-3. Analysis of Inflammation-Related Factor-Inhibiting Activity

Figure 11:
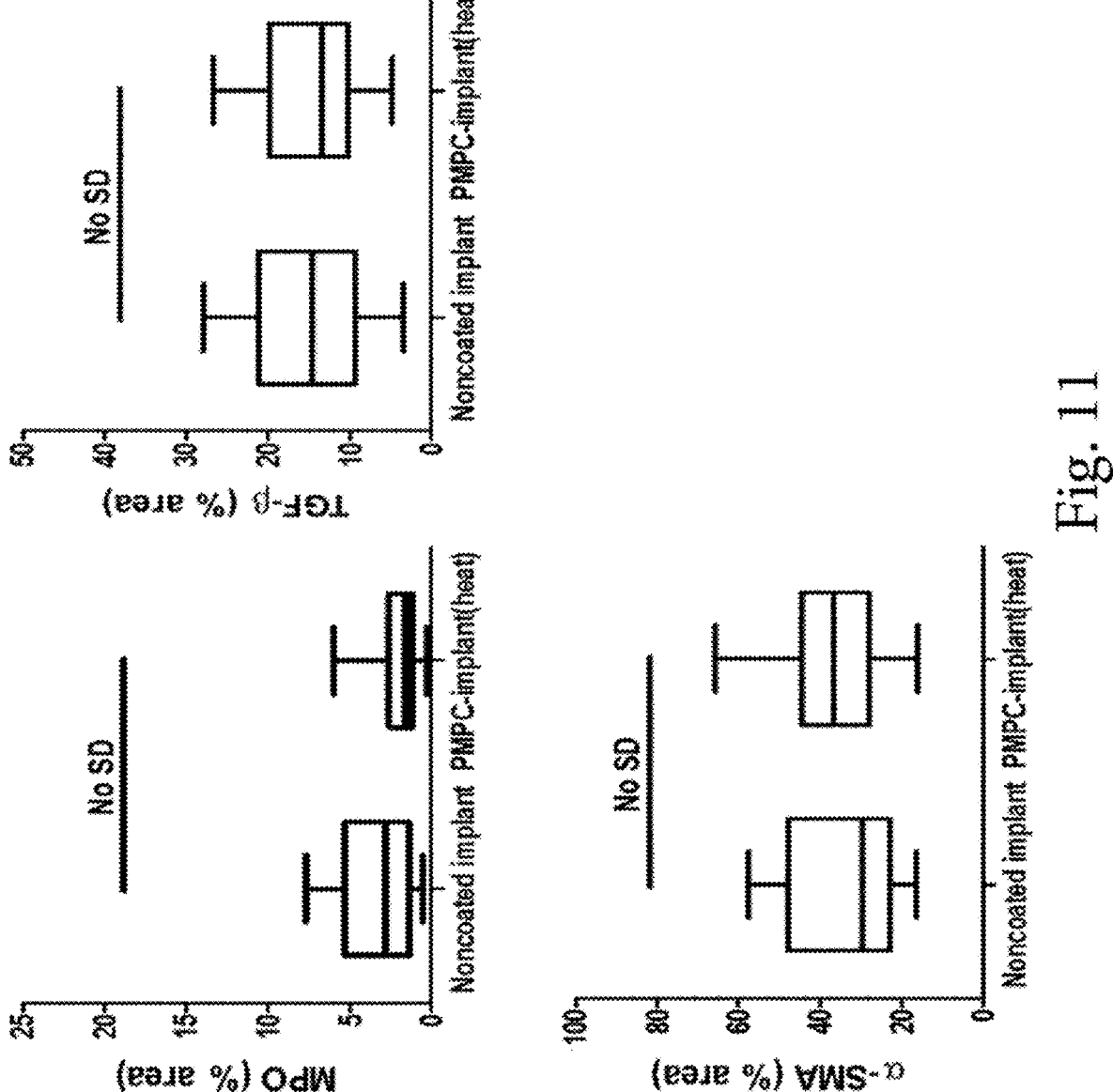
FIG. 11 shows expression levels of inflammation-related factors of an implant not coated with crosslinked PMPC and an implant coated with PMPC crosslinked using heat at 2 months after insertion into pigs.

Expression levels of transforming growth factor beta (TGF-β), which is an inflammation-related cytokine, myeloperoxidase (MPO), which is an enzyme present in granules of myelocyte-based cells, and alpha smooth muscle actin (α-SMA), which is a marker of myofibroblasts, were measured using immunohistochemistry (IHC) staining, and the results are shown in FIG. 11.

As shown in FIG. 11, it was confirmed that the implant coated with PMPC crosslinked using heat exhibited lower or similar expression levels of MPO, TGF-β, and α-SMA compared to those of the non-coated implant.

Example 7. Analysis of In Vivo Response (6-Month Large Animal Experiment)

Four implants not coated with crosslinked PMPC (non-coated) and four implants coated with PMPC crosslinked using heat (heat-coated) were prepared, sterilized using ethanol, and inserted under panniculus *carnosus* muscle of pigs in the same manner as in Example 6. After 24 weeks (6 months), capsules formed around the inserted implants were collected, and histopathological properties thereof were observed.

Example 7-1. Analysis of In Vivo Capsular Contracture-Inhibiting Activity

In order to identify in vivo capsular contracture-inhibiting activity, top and bottom sides of the capsule around the inserted implant were collected and stained via hematoxylin and eosin (H&E) staining to observe capsular thickness using a microscope. The capsular thickness was measured by dividing the capsule into three portions and measuring capsular thickness of each portion, and the results are shown in FIG. 12.

Figure 12:
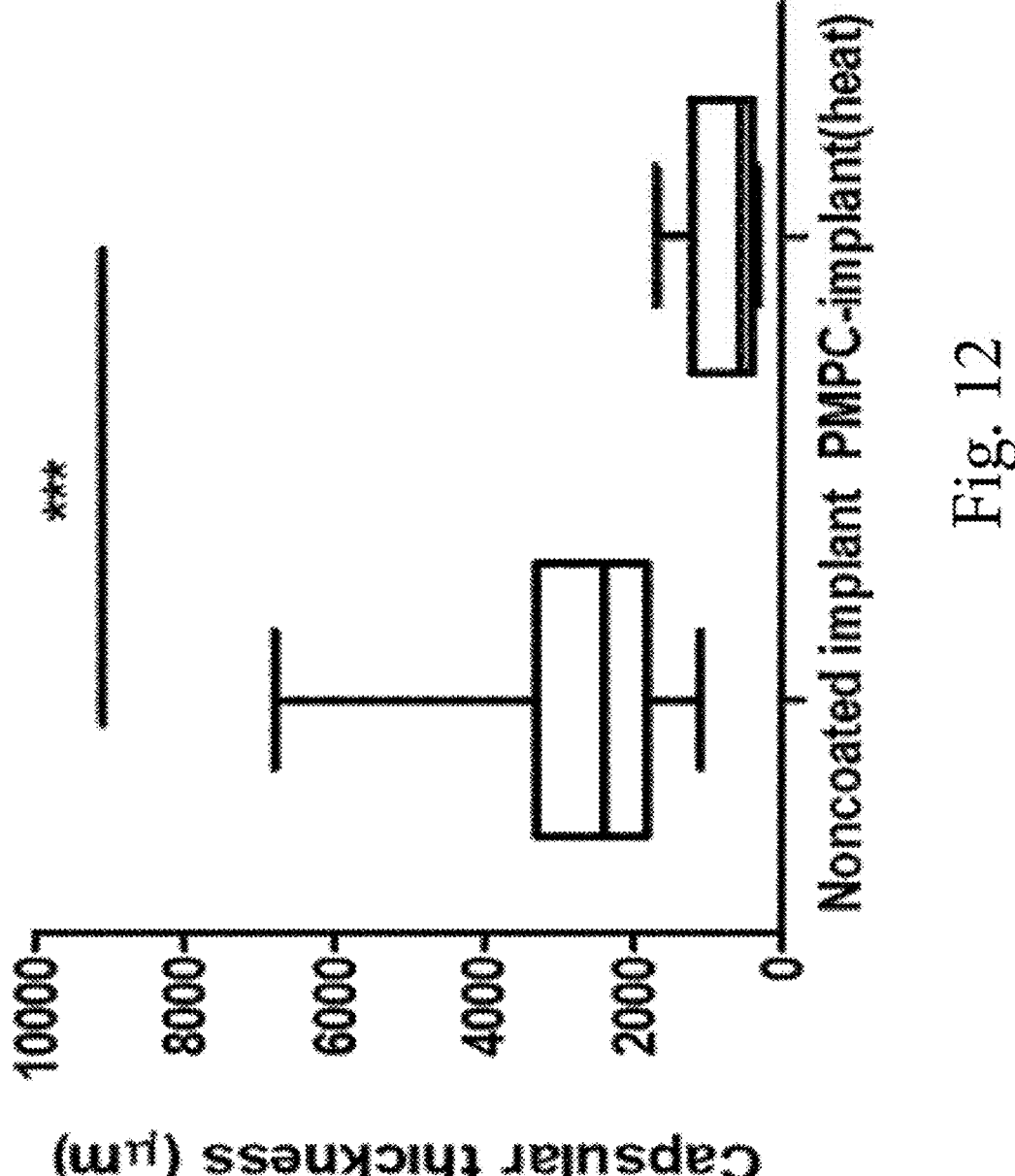
FIG. 12 shows capsular thickness on surfaces of an implant not coated with crosslinked PMPC and an implant coated with PMPC crosslinked using heat at 6 months after insertion into pigs.

As shown in FIG. 12, it was confirmed that an average thickness of the capsule formed on the surface of the implant coated with PMPC crosslinked using heat was decreased compared to an average thickness of the capsule formed on the surface of the non-coated implant.

Example 7-2. Analysis of Cellularity and Vascularity

Cellularity was measured by collecting tissues around the implant, staining the collected tissues, and calculating a sum of scores for inflammation-related cells such as lymphocytes, plasma cells, macrophages, and giant cells. Vascularity was measured by measuring the number of blood vessels via immunohistochemistry (IHC) staining using CD34 as an angiogenesis index. The results are shown in FIG. 13.

Figure 13:
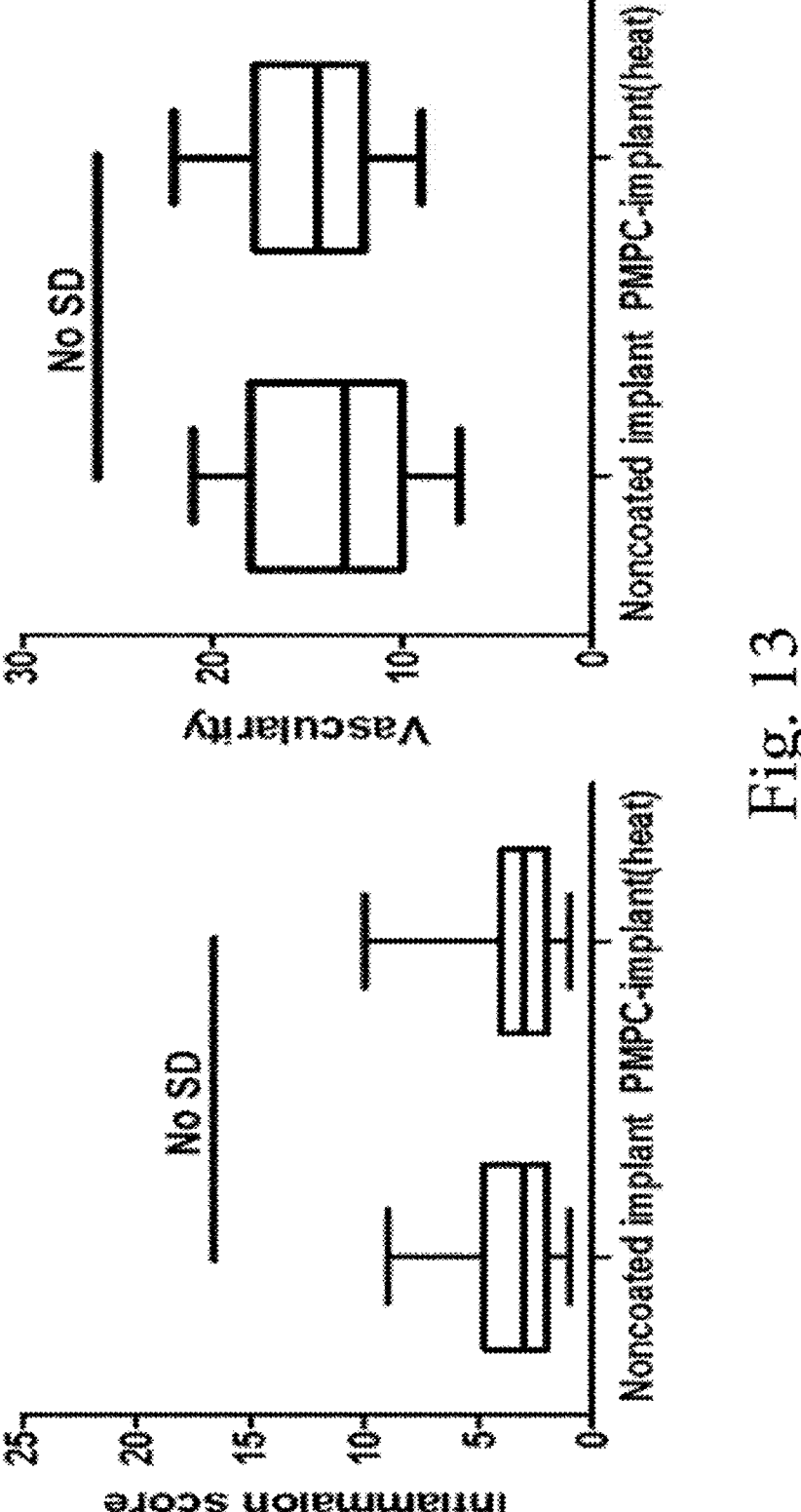
FIG. 13 shows cellularity and vascularity of an implant not coated with PMPC and an implant coated with PMPC crosslinked using heat at 6 months after insertion into pigs.

As shown in FIG. 13, it was confirmed that cellularity was decreased in both groups compared to that measured at Week 8 (2 months), and vascularity was increased in both groups compared to those measured at Week 8 (2 months).

Example 7-3. Analysis of Inflammation-Related Factor-Inhibiting Activity

Figure 14:
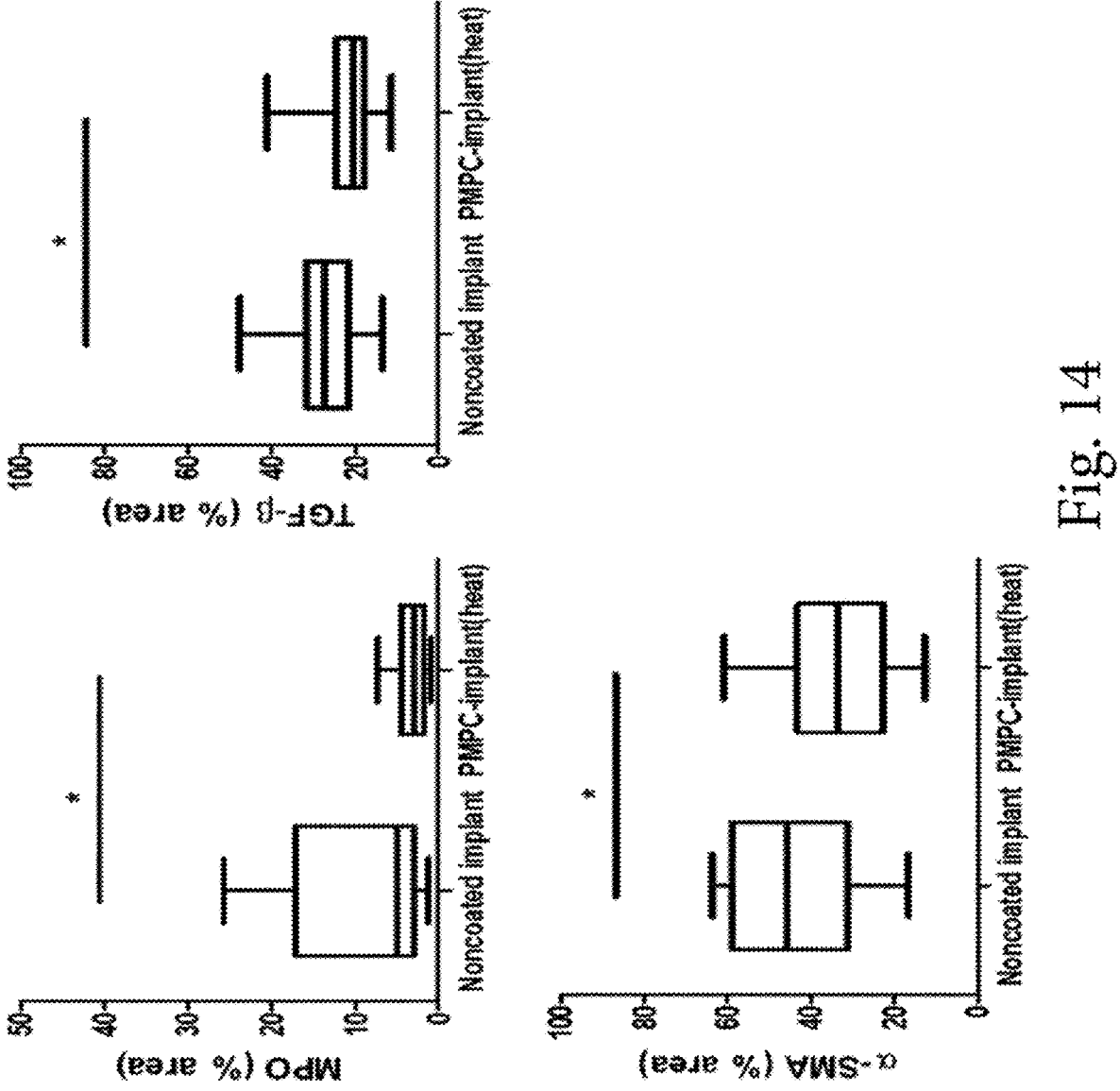
FIG. 14 shows expression levels of inflammation-related factors of an implant not coated with crosslinked PMPC and an implant coated with PMPC crosslinked using heat at 6 months after insertion into pigs.

Expression levels of transforming growth factor beta (TGF-β), which is an inflammation-related cytokine, myeloperoxidase (MPO), which is an enzyme present in granules of myelocyte-based cells, and alpha smooth muscle actin (α-SMA), which is a marker of myofibroblasts, were measured using IHC staining, and the results are shown in FIG. 14.

As shown in FIG. 14, the implant coated with PMPC crosslinked using heat exhibited significantly lower expression levels of MPO, which is a marker of inflammation, and TGF-β and α-SMA, which are criteria for inflammatory response and fibrous tissue formation, compared to those of the non-coated implant. These results are consistent with those of the experiment on capsular thickness, indicating that the implant coated with PMPC crosslinked using heat has a smaller capsular thickness compared to the non-coated implant since the expression of the fibrous tissue-forming cytokine decreases in accordance with the decreased inflammation response.

The above description of the present invention is provided for the purpose of illustration, and it would be understood by those skilled in the art that various changes and modifications may be made without changing the technical conception and essential features of the present invention. Thus, it is clear that the above-described embodiments are illustrative in all aspects and do not limit the present invention. Therefore, the scope of the disclosure is defined not by the detailed description, but by the claims and their equivalents, and all variations within the scope of the claims and their equivalents are to be construed as being included in the disclosure.

The invention claimed is:

1. A method for coating a breast implant for the reconstruction of breast or aesthetic augmentation, the method comprising:

allowing a thermal initiator and a first crosslinking agent to adsorb onto the implant and then drying the thermal initiator and the first crosslinking agent adsorbed on the implant, wherein the thermal initiator is selected from the group consisting of benzoyl peroxide (BPO), lauroyl peroxide, tert-butyl hydroperoxide, and cumene hydroperoxide (CHP); and after drying, adding a solution comprising an acrylate group-containing amphoteric monomer and a second crosslinking agent to the implant adsorbed with the thermal initiator and the first crosslinking agent and applying heat thereto, wherein the implant comprises a surface material selected from the group consisting of polydimethylsiloxane (PDMS), hydroxyapatite (HA), polylactic acid (PLA), polyglycolic acid (PGA), polytetrafluoroethylene (PTFE), polyethylene terephthalate (PET), polypropylene, polyamide, polyacetal, polyester, and polymethyl methacrylate, wherein the coating is formed by covalent bonds between acrylate groups of the acrylate group-containing amphoteric monomer and the surface material of the implant, wherein the coating provides strong hydrogen bonds with water molecules via its cationic and anionic charges to form a hydrated layer, wherein the concentration of the second crosslinking agent within the solution ranges from 0.01 mol % to 2.0 mol % relative to the amphoteric monomer, wherein heat is applied for 1 to 18 hours, wherein the first crosslinking agent and the second crosslinking agent are different and each independently selected from the group consisting of dipentaerythritol pentaacrylate, dipentaerythritol hexaacrylate, ethyleneglycol dimethacrylate, and a combination thereof, wherein the thermal initiator is used in an amount of 20 mol % to 50 mol % based on the acrylate group-containing amphoteric monomer, wherein the acrylate group-containing amphoteric monomer comprises at least one monomer selected from the group consisting of methacryloyloxyethyl phosphorylcholine (MPC), acryloyloxyethyl phosphorylcholine (APC), and carboxybetaine acrylate, and wherein the heat is applied at a temperature of 60° C. to 95° C.

2. The method of claim 1, wherein the step of allowing the thermal initiator and the first crosslinking agent to adsorb onto the implant comprises immersing the implant in a solution of the thermal initiator and the first crosslinking agent.

3. The method of claim 1, wherein the step of adding the solution comprising the acrylate group-containing amphoteric monomer and a second crosslinking agent to the implant adsorbed with the thermal initiator and the first crosslinking agent comprises immersing the implant adsorbed with the thermal initiator and the first crosslinking agent in a solution of the acrylate group-containing amphoteric monomer and the second crosslinking agent.

4. The method of claim 3, wherein heat is applied to the implant adsorbed with the thermal initiator and the first crosslinking agent while in the solution of the acrylate group-containing amphoteric monomer and the second crosslinking agent.

5. A method for coating a breast implant for the reconstruction of breast or aesthetic augmentation, the method comprising:

allowing a thermal initiator and a first crosslinking agent to adsorb onto the implant and then drying the thermal initiator and the first crosslinking agent adsorbed on the implant, wherein the thermal initiator is benzoyl peroxide (BPO); and after drying, adding a solution comprising an acrylate group-containing amphoteric monomer and a second crosslinking agent to the implant adsorbed with the thermal initiator and the first crosslinking agent and applying heat thereto, wherein the implant comprises a surface material selected from the group consisting of polydimethylsiloxane (PDMS), hydroxyapatite (HA), polylactic acid (PLA), polyglycolic acid (PGA), polytetrafluoroethylene (PTFE), polyethylene terephthalate (PET), polypropylene, polyamide, polyacetal, polyester, and polymethyl methacrylate, wherein the coating is formed by covalent bonds between acrylate groups of the acrylate group-containing amphoteric monomer and the surface material of the implant, wherein the coating provides strong hydrogen bonds with water molecules via its cationic and anionic charges to form a hydrated layer, wherein the concentration of the second crosslinking agent within the solution ranges from 0.01 mol % to 2.0 mol % relative to the amphoteric monomer, wherein heat is applied for 1 to 18 hours, wherein the first crosslinking agent and the second crosslinking agent are different and each independently selected from the group consisting of dipentaerythritol pentaacrylate, dipentaerythritol hexaacrylate, and a combination thereof, wherein the thermal initiator is used in an amount of 20 mol % to 50 mol % based on the acrylate group-containing amphoteric monomer, wherein the acrylate group-containing amphoteric monomer comprises at least one monomer of methacryloyloxyethyl phosphorylcholine (MPC), and wherein the heat is applied at a temperature of 60° C. to 95° C.

6. The method of claim 5 wherein the step of allowing the thermal initiator and the first crosslinking agent to adsorb onto the implant comprises immersing the implant in a solution of the thermal initiator and the first crosslinking agent.

7. The method of claim 5 wherein the step of adding the solution comprising the acrylate group-containing amphoteric monomer and a second crosslinking agent to the implant adsorbed with the thermal initiator and the first crosslinking agent comprises immersing the implant adsorbed with the thermal initiator and the first crosslinking agent in a solution of the acrylate group-containing amphoteric monomer and the second crosslinking agent.

8. The method of claim 7, wherein heat is applied to the implant adsorbed with the thermal initiator and the first crosslinking agent while in the solution of the acrylate group-containing amphoteric monomer and the second crosslinking agent.

* * * * *